(12) United States Patent
Wang et al.

(10) Patent No.: US 6,252,925 B1
(45) Date of Patent: Jun. 26, 2001

(54) SYSTEM AND METHOD FOR PERFORMING COMPUTED TOMOGRAPHY WITH FIBER WAVEGUIDES

(75) Inventors: Weiping Wang, Schenectady; Christopher Donald Johnson, Clifton Park, both of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/351,796

(22) Filed: Jul. 13, 1999

Related U.S. Application Data

(63) Continuation-in-part of application No. 08/905,761, filed on Aug. 4, 1997, now abandoned.

(51) Int. Cl.$^7$ .................................................. G01N 23/00
(52) U.S. Cl. .................................................. 378/10; 378/4
(58) Field of Search ............................................ 378/4, 10

(56) References Cited

PUBLICATIONS

H. Goldberg, et al, "Evaluation of Ultrafast CT Scanning of the Adult Abdomen", Investigative Radiology, vol. 24, 1989, pp. 537–543.

T. Iinuma, et al, "Proposed System for Ultrafast Computed Tomography", Journal of Computer Assisted Tomography, vol. 1, No. 4, 1977, pp. 494–499.

C. MacDonald, et al, "Medical Applications of Polycapillary X–ray Optics", SPIE vol. 2519, 1995, pp. 1–11.

M. Kumakhov, "Channeling of Photons and New X–ray Optics", Nuclear Instruments and Methods in Physics Research, B48, 1990, pp. 283–286.

L. Wang, et al, "Measurement of Capillary Optic Performance for Hard X–rays", SPIE, vol. 2519, pp. 218–223.

*Primary Examiner*—Craig E. Church
(74) *Attorney, Agent, or Firm*—David C. Goldman; Jill M. Breedlove

(57) ABSTRACT

A system and method for performing computed tomography without having to use a complicated mechanical device to move an x-ray source about an object being scanned. Instead, this invention uses flexible waveguides such as optical fibers to direct the x-ray beams generated from the x-ray source. The waveguides direct the x-ray beam to the object at predetermined orientations and distances. A multiplexing unit optically coupled to the x-ray source and the waveguide, steers the x-ray energy from the x-ray energy source to the waveguide.

19 Claims, 5 Drawing Sheets

SYSTEM AND METHOD FOR PERFORMING COMPUTED TOMOGRAPHY WITH FIBER WAVEGUIDES

This application is a CIP of Ser. No. 08/905,761, filed Aug. 4, 1997, now Abandoned.

BACKGROUND OF THE INVENTION

The present invention relates generally to computed tomography and more particularly to performing high speed x-ray computed tomography with fiber waveguides.

In computed tomography, an x-ray source projects a fan-shaped beam at an object being imaged, such as a medical patient or an engineered part. The intensity of the transmitted radiation is dependent upon the attenuation of the x-ray beam by the object. The x-ray beam passes through the object and impinges upon an array of radiation detectors. Each detector in the array produces a separate electrical signal that is a measurement of the beam attenuation. The attenuation measurements from all of the detectors are acquired separately to produce a transmission profile.

In a conventional x-ray computed tomography (CT) system, the x-ray source and detector array are rotated on a gantry within the imaging plane and around the object, so that the angle at which the x-ray beam intersects the object constantly changes. A group of x-ray attenuation measurements from the detector array at a given angle is referred to as a "view". A "scan" of the object represents a set of views made at different angular orientations during one revolution of the x-ray source and the detector. The data for a given scan is stored in memory as a two-dimensional array with storage locations along one axis of the array representing the data from each radiation detector and the storage locations along the other axis containing data for the different views. The scan data is then processed to construct an image that corresponds to a two-dimensional slice taken through the object. A series of two-dimensional slices are used to form a three-dimensional scan.

A problem with the conventional CT system is that its use in medical and industrial applications is limited by the speed of the x-ray source and the gantry that is used to rotate the source around the object being imaged. In particular, for medical applications, the gantry rotates the x-ray source around the object at a scan cycle ranging from about 0.5 seconds to about 1.0 seconds. The x-ray source uses x-ray tube inserts that have rotating target velocities ranging between 2000RPM and 9000 RPM. The dynamic forces resulting from moving a rotating target within a tube limit the gantry rotational speed. In addition to constraining scanning speed, the dynamic forces decrease the life of the x-ray tube and increase the amount of service needed to maintain the CT system. Typically, these x-ray tubes are limited to about 100,000 to about 200,000 scans. As a result of the decreased x-ray tube life and increased service, the overall reliability of the CT system for medical applications is jeopardized over time. In industrial applications, the conventional CT system has its limitations in viewing certain rotating components under load and for nondestructive testing of new designs. Viewing a component's internal mechanical integrity while under load is useful for design verification and optimization, quality assurance, and preventative maintenance. With the conventional CT system, incipient flaws and structural integrity are difficult to identify. Accordingly, there is a need for a faster, mechanically simpler, and more reliable CT system that can be used for medical and industrial applications.

SUMMARY OF THE INVENTION

In accordance with this invention, there is provided a system and method for performing CT that is faster, mechanically simple, and more reliable for medical and industrial applications. Instead of using a complicated mechanical device for moving the delicate x-ray vacuum tube, this invention uses flexible waveguides such as optical fibers to concentrate and direct the x-ray beams generated from the x-ray tube. The waveguides direct the x-ray beam to the object to be scanned at predetermined orientations and distances.

Thus, in accordance with one embodiment of this invention, there is provided a system and method for performing x-ray computed tomography of an object. In this embodiment, an x-ray energy source emits x-ray energy towards the object. A waveguide directs the x-ray energy from the x-ray energy source to the object at a plurality of predetermined orientations. A detector acquires x-ray energy passing through the object, wherein the x-ray energy acquired on the detector is x-ray projection data.

In accordance with a second embodiment of this invention, there is provided a system and method for performing x-ray computed tomography of an object. In this invention, an x-ray energy source emits x-ray energy towards the object. A waveguide directs the x-ray energy from the x-ray energy source to the object at a plurality of predetermined orientations. A multiplexing unit optically coupled to the x-ray energy source and the waveguide, steers the x-ray energy from the x-ray energy source to the waveguide.

DETAILED DESCRIPTION OF THE INVENTION

Figure 1:
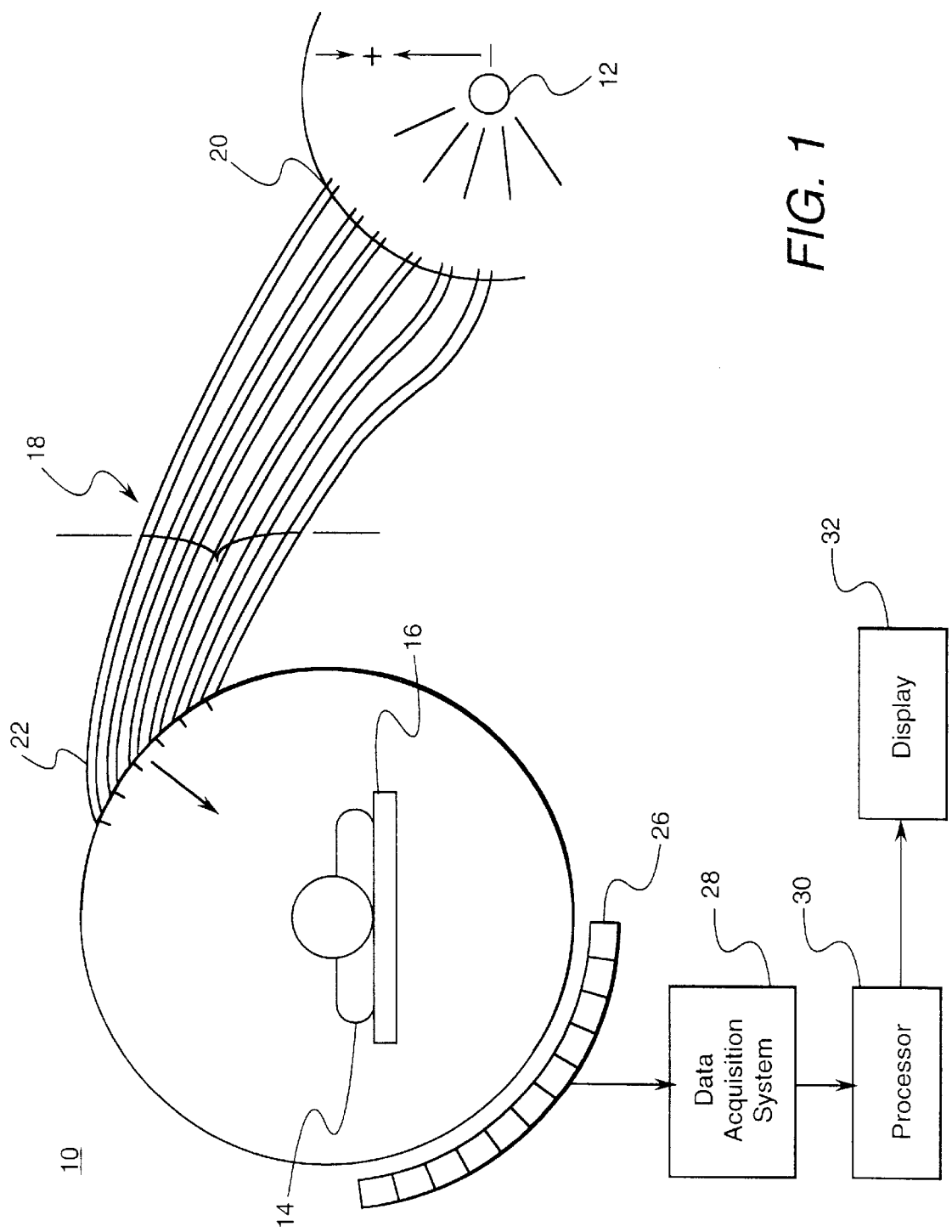
FIG. 1 shows a schematic of a x-ray CT system according to one embodiment of this invention.

FIG. 1 shows a schematic of a x-ray CT system 10 according to this invention. The x-ray CT system 10 includes a stationary x-ray energy source 12 that emits x-ray energy towards an object 14 such as a medical patient or an engineered part. In the illustrative embodiment, the object 14 is a medical patient. The patient is secured to the x-ray CT system by a position table 16 such as a one-dimensional linear motion table. In industrial type applications, the component under inspection is secured to the x-ray CT system by a fixturing device.

A waveguide 18 directs the x-ray energy from the x-ray energy source 12 to the object 14 at a plurality of predetermined orientations. The waveguide 18 comprises a plurality of collimated optical fibers such as hollow core capillaries and geometric sections having total internal reflection. The hollow core capillaries are held together by a plate with a grid pattern of holes drilled on it. Each hollow core capillary passes through a hole and is held in position by the hole. The refraction index of each hollow core capillary center is higher than that of the solid wall for the x-ray wavelength. Thus, given the wavelength of the x-ray, the inside and outside diameters of the hollow core capillaries can be tailored such that the x-ray can be confined within the capillary by total reflection. Since these capillaries are small in diameter, they can be routed to a desired location and orientation for 360 degree scanning.

The plurality of hollow core capillaries are constructed from dense materials such as Borosilicate, whose radius of curvature does not exceed $d/\phi^{2\kappa}$, wherein d is the channel diameter and $\phi_\kappa$ is the fennel reflection angle. it has been shown that energy from 0.1 KeV to 10 MeV (i.e., the x-ray and gamma-ray range) can be reflected and conveyed, with losses up to 60% at 60 KeV, via total external reflection within a curved 750 mM OD, 22 mM channel capillary tube. A more detailed description of the hollow core capillaries is provided in Kumakhov, "Channeling of Photons and New X-Ray Optics," Nuclear Instruments and Methods in Physics Research, (1990) pp. 283–286 and Wang et al., "Measurement of Capillary Optic Performance for Hard X-Rays," Spie, (July 1995) pp. 218–223, both of which are incorporated herein by reference.

One end of the waveguide 18 is referred to as a concentrator and is shown as element 20. The concentrator 20 is the portion of the waveguide 18 that takes the form of a one-dimensional array and aligns the plurality of hollow core capillaries to the x-ray energy source 12. Essentially, the concentrator 20 increases the effective density of the x-ray beam emitted from the x-ray energy source 12. The concentrator 20 increases the effective density of the x-ray beam by expanding the aperture from the x-ray energy source 12, collimating lower energy density signals which would otherwise be lost within the source or absorbed by beam normalizing filters, and then focusing the x-ray energy into a uniform front. The result is a more uniform energy distribution at a higher mean energy level per unit area.

The end opposite of the concentrator 20 is referred to as a director 22. The director 22 collects the x-ray energy in the capillaries and directs the x-ray energy to the object at the plurality of predetermined orientations for a complete 360 degree scanning. The director 22 is preferably ring shaped, however, it can take the form of other shapes. Basically, the director is a mechanical hold that securely attaches the ends of the each of the capillaries and aims them at the object being scanned.

A detector 26 detects the x-ray energy passing through the patient 14. In the illustrative embodiment, the detector 26 is a one-dimensional array, however a two-dimensional array is within the scope of this invention. X-ray energy passing through the patient is detected by the detector as x-ray projection data. The x-ray projection data is converted to corresponding electrical signals and sent to a data acquisition system 28, which registers the electrical signals. The electrical signals corresponding to the x-ray projection data in the data acquisition system 28 are then sent to a processor 30 for reconstructing a three-dimensional CT image of the patient 14 from the x-ray projection data using known reconstruction algorithms. The reconstructed image is then sent from the processor 30 to a display 32, which displays the three-dimensional CT image of the patient 14.

One advantage of the system 10 is that the waveguide 18 can direct the x-ray energy closer to the object being scanned than a conventional system. The waveguide 18 can adaptively direct the x-ray energy closer to the object because the CT system is no longer limited by the constraint of a x-ray tube attached to an orbiting mechanism such as a gantry device in a conventional system. The improvement in efficiency resulting from having the x-ray energy closer to the object could lead to reduced exposure time in addition, since the system 10 is not limited by the speed and movement of an orbiting mechanism, this invention is able to provide new flexibility in CT system design, including options of having multiple x-ray sources and using non-circular scanning patterns.

Figure 2:
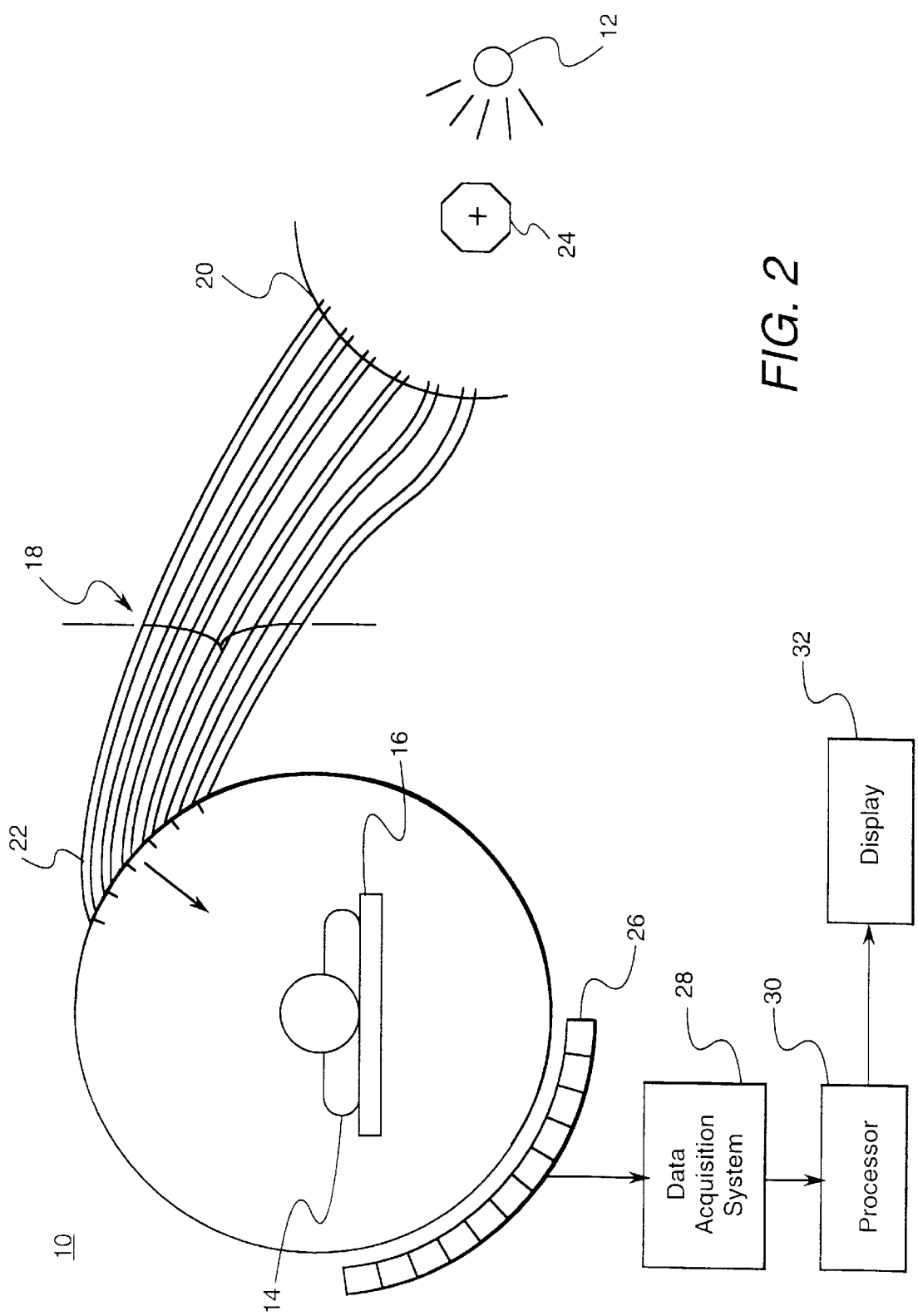
FIG. 2 shows a schematic of a x-ray CT system according to a second embodiment of this invention.

FIG. 2 shows a schematic of the x-ray CT system 10 according to another embodiment. In this embodiment, the x-ray CT system 10 includes a multiplexing unit 24 optically coupled to the x-ray energy source 12 and the waveguide 18. The multiplexing unit 24 steers the x-ray energy from the x-ray energy source 12 to the waveguide 18, which directs the x-ray energy to the patient 14.

Figure 3:
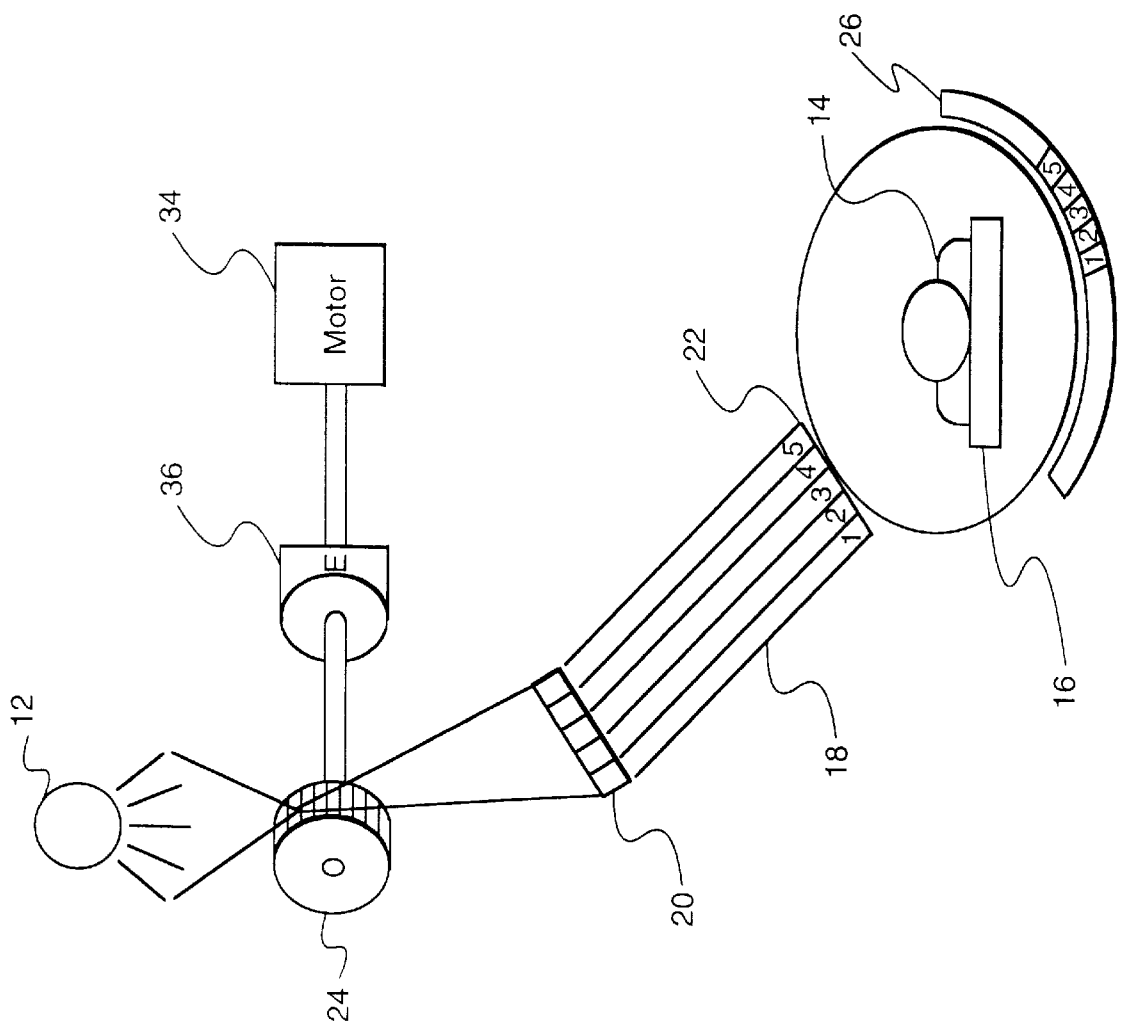
FIG. 3 shows a more detailed schematic of the rotating polygon mirror used in FIG. 2.

One alternative of this embodiment is to use a rotating polygon mirror of low mass for the multiplexing unit 24. The polygon mirror's low mass facilitates a high speed precision scanning rotation pattern. FIG. 3 shows a more detailed schematic of the rotating polygon mirror used in the CT system 10. The rotating polygon mirror 24 is driven by a dedicated drive motor system 34 and monitored for speed and angular displacement by a high speed, high resolution encoder 36. In operation, the rotating polygon mirror 24 steers the incident of the x-ray energy sequentially towards the concentrator end 20 of the waveguide 18 of the collimated capillaries. The capillaries then transmit the x-ray energy to the different locations residing in the director 22.

In this embodiment, the surfaces of the polygon mirror only "reflects" x-ray level energy at a grazing incidence of $\omega_p/\omega$, wherein $\omega_p$ is the plasma frequency and $\omega$ is the photon frequency. The x-ray level energy reflected at this grazing incidence is steered through the target capillaries aperture of the waveguides. All other greater angles will allow the source x-ray energy to pass directly through or be absorbed. Because this non-reflected energy is not aligned with the target capillaries aperture of the waveguides, it is not allowed to be part of the target emit/detect sequence.

The x-ray energy is directed from the director 22 towards the patient 14. The x-ray energy passes through the patient 14 and is detected by the detector 26, such that each x-ray projection data point is a discrete digitally mapped location from the locations residing in the director 22. For example, referring to FIG. 3, the x-ray energy in locations 1 and 2 in the director 22 are mapped to locations 1 and 2 in the detector 26. During rotation of the polygon mirror 24, each side of the mirror constitutes a complete scan cycle. Thus, the actual scanning rate of the CT system 10 is N times the rotational speed of the mirror, where N is the number of sides of the polygon.

Figure 4:
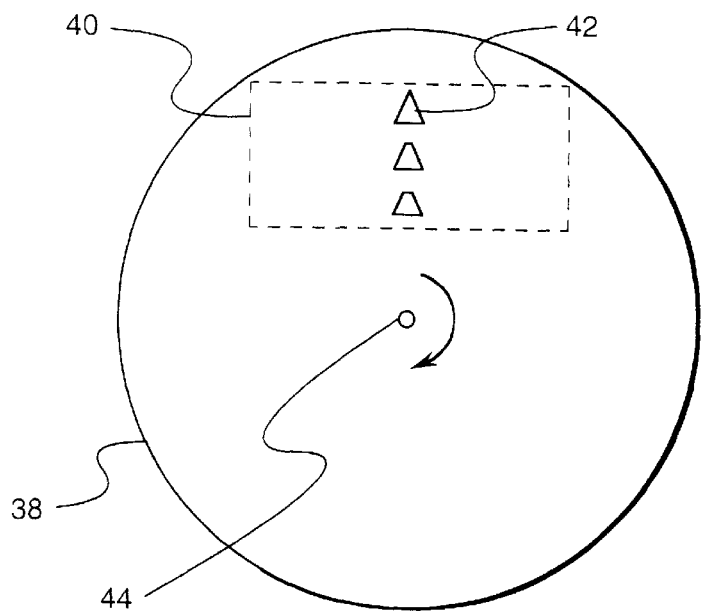
FIG. 4 shows a schematic of a top view of a rotating aperture disk used in a x-ray CT system according to an alternative embodiment of FIG. 2.

Another alternative of this embodiment is to use a rotating aperture disk in place of the rotating polygon mirror 24 to steer the x-ray energy from the x-ray energy source 12 to the waveguide 18. FIG. 4 shows a schematic of a top view of a rotating aperture disk 38 used in the CT system 10. The rotating aperture disk 38 is preferably an energy absorbing medium such as lead. The aperture disk 38 has a source exposure area 40 with a plurality of apertures 42 therein which rotates about a shaft 44. Each of the apertures 42 in the disk 38 have a constant pass through density for selectively exposing x-ray energy from the x-ray energy source 12 to the waveguide 18.

Figure 5:
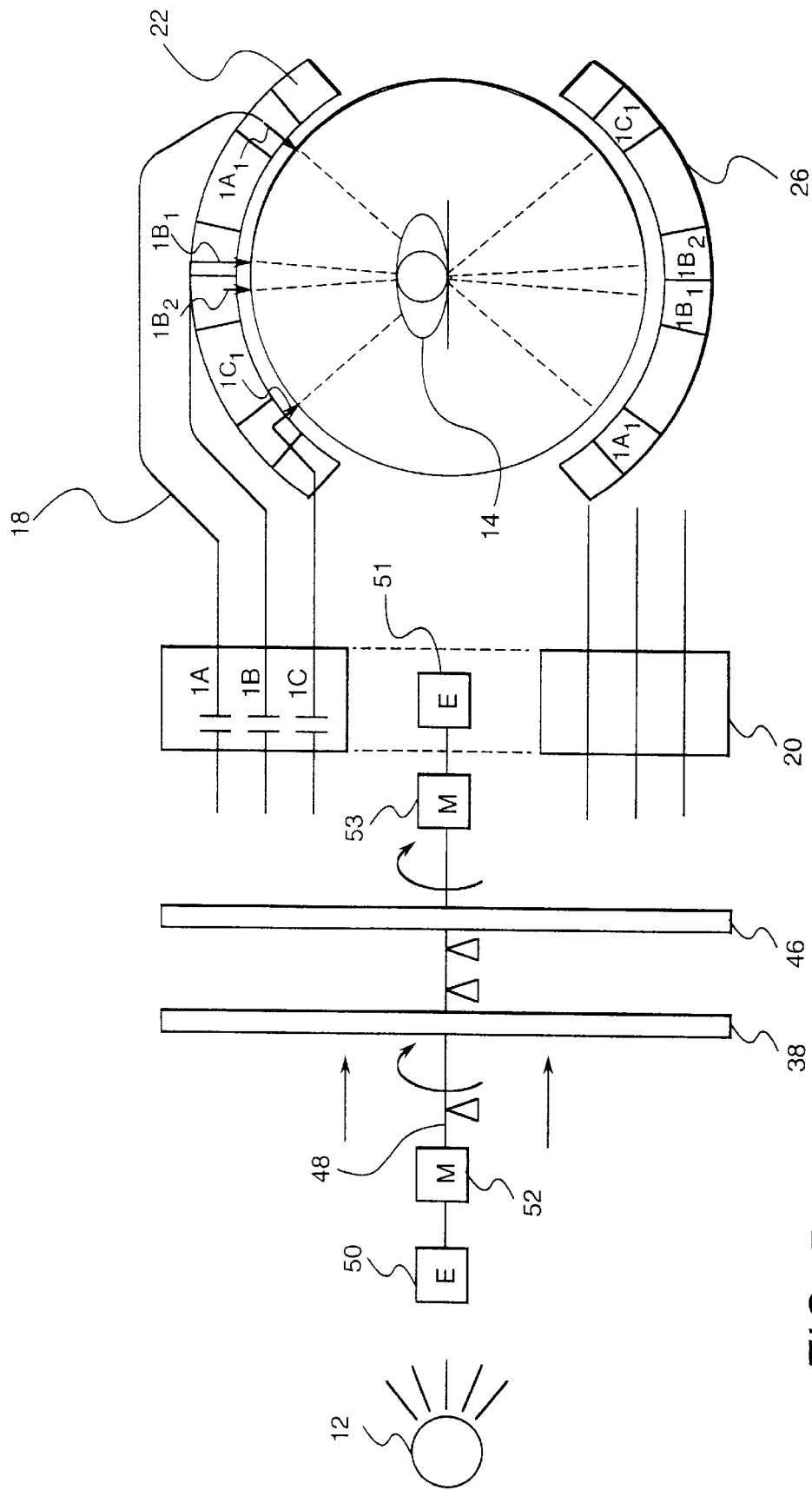
FIG. 5 shows a schematic of the rotating aperture disk used in the x-ray CT system according to the alternative embodiment of FIG. 2.

FIG. 5 shows a schematic of the rotating aperture disk 38 used in the CT system 10. In FIG. 5, the total internal reflecting waveguides 18, set up in a two-dimensional matrix (i.e., 1A, 1B, and 1C), are exposed through an aperture effectively created by the rotating aperture disk 38 and another rotating, energy absorbing, disk 46 having a plurality apertures. Both disks 38 and 46 have the capability to be rotated independently of each other. The rotating aperture disk 38 allows x-ray energy to pass through its apertures 42 onto the disk 46. The rotating aperture disk 38 is driven by a dedicated drive motor system 52 and is monitored for speed and angular displacement by a high speed, high resolution encoder 50. The disk 46 is a strobe disk and has its own drive motor system 53 and position encoder 51. The strobe disk is driven such that an opening is created which exposes the one-dimensional receiving end 20 of the waveguide to the x-ray energy. The effective aperture may expose no energy if the two disks 38 and 46 are rotated at constant speed, but offset by the width of their respective apertures 42. Full energy passes through when both the disks 38 and 46 are rotated at constant speed with the apertures fully aligned. Beat frequencies or partial exposures are also facilitated by the two independently rotating disks 38 and 46.

In operation, the aperture disk 38 and the strobe disk 46 selectively expose x-ray energy from the x-ray energy source 12 to the waveguide 18 by steering the incident of the x-ray energy passing through the apertures sequentially towards the receiving end of the capillaries. The capillaries then transmit the x-ray energy to the different locations residing in the director 22. The x-ray energy is directed from the director 22 towards the patient 14. The x-ray energy passes through the patient 14 and is detected by the detector 26, such that each x-ray projection data point is a discrete digitally mapped location from the locations residing in the director 22. For example, referring to FIG. 5, the x-ray energy in locations 1A, 1B, and 1C in the director 22 are mapped to locations 1A, 1B, and 1C in the detector 26. The actual scanning rate of the CT system 10 shown in FIG. 5 is the rotational speed of the aperture disk 38 multiplied by the number of apertures 42 and waveguide overleaf arrangements, which is a two-dimensional surface of collimated capillaries which can be arranged so as to increase slice thickness, or concentrate the x-ray energy, or increase the fan beam.

An advantage associated with the x-ray CT system disclosed in both embodiments of this invention, is that a gantry is not used to rotate the x-ray source 12 around the patient 14. Therefore, the x-ray tube inserts in the x-ray source are not subject to the high dynamic loads that constrain scan speed and eventually decrease its life and increase the amount of service needed to maintain the CT system. The scan time in this invention will be reduced because there is no gantry being used. In particular, the scan time in this invention will be reduced from a period ranging from 0.5 to 1.0 seconds to a period ranging from about 0.01 to 0.5 seconds.

Figure 6:
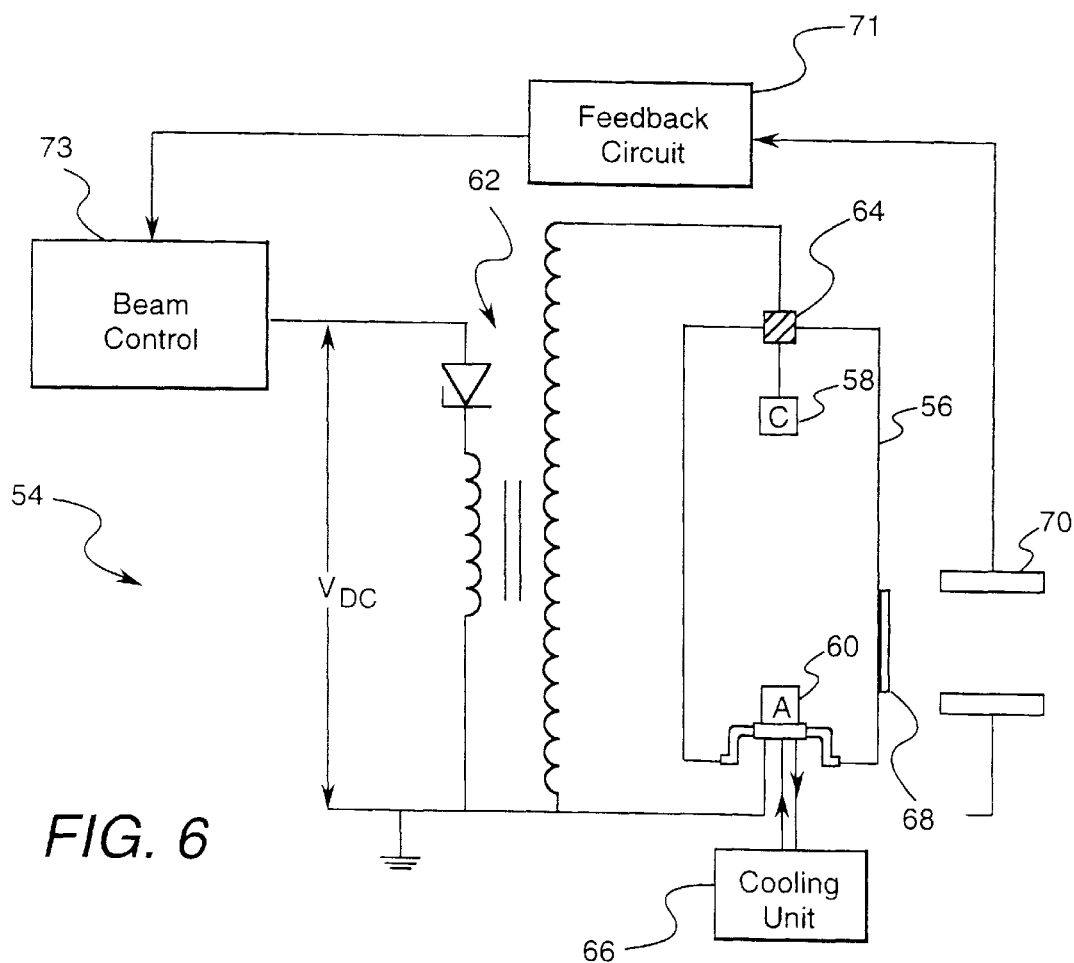
FIG. 6 shows a schematic of a static x-ray tube used in this invention.

Instead of using a rotating x-ray source, it is within the scope of this invention to use a static x-ray tube with the x-ray CT system of the first embodiment and second embodiment. FIG. 6 shows a schematic of a static x-ray tube 54. The static x-ray tube includes a vacuum tube 56 having a cathode 58 at one end and a stationary anode 60 at an end opposite of the cathode. A transformer 62 is used to produce a high voltage that penetrates the vacuum tube 56 at an opening 64. The transformer 62 is a high voltage, low inductance type transformer. The high voltage causes the cathode 58 to produce electron beams that are incident on the anode 60. Coolant is pumped in and out of the vacuum tube 56 at the anode 60 by a cooling unit 66 in order to dissipate the high thermal energy arising therein. X-ray energy exits the vacuum tube 56 through a window 68 and is directed to the concentrator, the multiplexing unit, the waveguide, the patient, and the detector. An electromagnetic sensor 70 located about the window 68 is used to monitor x-ray energy strength and uniformity. The output signal generated from the electromagnetic sensor 70 is sent to a feedback control circuit 71, which feeds back a control signal to a beam control unit 73 which is used to vary the excitation of the vacuum tube 56.

The x-ray CT system of this invention is well suited for medical and industrial applications. For example, medical applications would utilize the rapid scan speed of this invention for enhanced resolution, multi-slice or three-dimensional viewing of patients and organs that are moving too rapidly for convention CT scanning, low dose applications such as those that would be requisite for use during surgery or for more frequent scans to monitor healing progress or for tissue irradiation. In addition, this invention could be used in surgical procedures for noninvasive or minimally invasive procedures and those procedures that afford limited direct view or access by a surgeon. For industrial applications, the rapid scan speed of this invention could be used to strobe bodies in motion under actual service conditions and for design verification and prototype tests.

It is therefore apparent that there has been provided in accordance with the present invention, a system and method for performing three-dimensional x-ray computed tomography scanning of an object system that fully satisfy the aims and advantages and objectives hereinbefore set forth. The invention has been described with reference to several embodiments, however, it will be appreciated that variations and modifications can be effected by a person of ordinary skill in the art without departing from the scope of the invention.

What is claimed is:

1. A x-ray computed tomography system for three-dimensional scanning of an object, comprising:

an x-ray energy source;

a waveguide for directing x-ray energy from the x-ray energy source to the object at a plurality of predetermined orientations; and a multiplexing unit optically coupled to the x-ray energy source and the waveguide for steering x-ray energy from the x-ray energy source to the waveguide.

2. The system according to claim 1, wherein the waveguide is a plurality of collimated optical fibers.

3. The system according to claim 2, wherein one end of the plurality of collimated optical fibers forms an array for receiving x-ray energy being steered from the multiplexing unit and directing the x-ray energy into different fibers in the plurality of collimated optical fibers.

4. The system according to claim 3, wherein another end of the plurality of collimated optical fibers forms a director for collecting x-ray energy from within the plurality of collimated optical fibers and directing the x-ray energy to the object at the plurality of predetermined orientations.

5. The system according to claim 1, wherein the multiplexing unit comprises a rotating polygon mirror, wherein the polygon mirror steers x-ray energy from the x-ray energy source sequentially to the waveguide.

6. The system according to claim 1, wherein the multiplexing unit comprises at least one rotating aperture disk having a plurality of apertures for selectively exposing x-ray energy from the x-ray energy source to the waveguide.

7. The system according to claim 1, further comprising a detector for acquiring x-ray energy passing through the object, the x-ray energy acquired on the detector as x-ray projection data.

8. The system according to claim 7, further comprising a processor for reconstructing an image of the object from the x-ray projection data.

9. The system according to claim 1, wherein the x-ray energy source is a static x-ray tube.

10. A method for performing three-dimensional x-ray computed tomography scanning of an object with an x-ray energy source, a waveguide, and a multiplexing unit optically coupled to the x-ray energy source and the waveguide, comprising:

emitting x-ray energy from the x-ray energy source;

steering the x-ray energy from the x-ray energy source to the waveguide with the multiplexing unit; and directing the x-ray energy from the waveguide to the object at a plurality of predetermined orientations.

11. The method according to claim 10, wherein the waveguide is formed from a plurality of collimated optical fibers.

12. The method according to claim 11, wherein one end of the plurality of collimated optical fibers forms an array for receiving x-ray energy being steered from the multiplexing unit and directing the x-ray energy into different fibers in the plurality of collimated optical fibers.

13. The method according to claim 12, further comprising collecting the x-ray energy from the plurality of collimated optical fibers and directing the x-ray energy to the object at the plurality of predetermined orientations.

14. The method according to claim 10, wherein the multiplexing unit comprises a rotating polygon mirror, wherein the polygon mirror steers x-ray energy from the x-ray energy source sequentially to the waveguide.

15. The method according to claim 10, wherein the multiplexing unit comprises at least one rotating aperture disk having a plurality of apertures for selectively exposing x-ray energy from the x-ray energy source to the waveguide.

16. The method according to claim 10, further comprising detecting x-ray energy passing through the object with a detector, the x-ray energy acquired on the detector as x-ray projection data.

17. The method according to claim 16, further comprising reconstructing an image of the object from the x-ray projection data with a processor.

18. The method according to claim 10, wherein the x-ray energy source is a static x-ray tube.

19. The method according to claim 10, further comprising concentrating the x-ray energy from the x-ray source to a more concentrated and uniform x-ray energy front.

* * * * *